United States Patent [19]

Chiquet

[11] 4,273,116
[45] Jun. 16, 1981

[54] DEVICE FOR EXTERNAL FIXATION OF BONE FRAGMENTS

[76] Inventor: Claude Chiquet, Morystrasse 77, 4125 Riehen, Switzerland

[21] Appl. No.: 52,247

[22] Filed: Jun. 26, 1979

[30] Foreign Application Priority Data

Jun. 27, 1978 [CH] Switzerland .................. 7007/78

[51] Int. Cl.³ .................. A61F 5/04; F16 3/00; F16C 11/06; F16D 1/12
[52] U.S. Cl. .................. 128/92 A; 128/92 BA; 403/90; 403/131
[58] Field of Search .................. 128/92 A, 92 R, 92 B, 128/92 BA, 92 E, 92 EA; 403/76, 77, 90, 131, 141, 122

[56] References Cited

U.S. PATENT DOCUMENTS

| 348,978 | 9/1886 | Keilholtz | 403/77 |
|---|---|---|---|
| 1,574,899 | 3/1926 | Kellogg | 403/90 |
| 1,864,534 | 6/1932 | Gulesian | 403/90 |
| 2,110,414 | 3/1938 | Bell | 128/84 |
| 2,238,869 | 4/1941 | Haynes | 128/92 |
| 2,238,870 | 4/1941 | Haynes | 128/92 A |
| 2,346,346 | 4/1944 | Anderson | 128/92 A |
| 2,391,537 | 12/1945 | Anderson | 128/84 |
| 2,391,693 | 12/1945 | Ettinger | 128/84 |
| 2,652,221 | 9/1953 | Kampa | 403/76 |
| 3,308,812 | 3/1967 | Gidloud | 128/92 R |
| 3,961,854 | 6/1976 | Jaquet | 128/92 A |
| 4,127,119 | 11/1978 | Kronner | 128/92 A |
| 4,135,505 | 1/1979 | Day | 128/92 A |

FOREIGN PATENT DOCUMENTS

| 203544 | 6/1939 | Switzerland | 128/92 A |
|---|---|---|---|
| 100688 | 12/1916 | United Kingdom | 128/84 |
| 401357 | 2/1974 | U.S.S.R. | 128/92 A |
| 445423 | 5/1975 | U.S.S.R. | 128/92 A |

OTHER PUBLICATIONS

"Osteotaxis"-Catalog No. (HJL012D), Apr. 1977, by Jaquet Freres, Geneva, Switzerland.

Primary Examiner—Robert W. Michell
Assistant Examiner—C. W. Shedd
Attorney, Agent, or Firm—Caspar C. Schneider, Jr.; David M. McConoughey

[57] ABSTRACT

An external fixation device for reducing fractures and realigning bones comprises sliding universal articulated couplings for enabling easy adjustment and subsequent locking of connections between Steinmann pins and tubular tie-rods. The couplings each include a split, spherical adapter sleeve which is embraced by the matching inner surface of an open ring portion of a coupling locking clamp having clamp lugs tightenable against a block by means of a nut-and-bolt assembly. Further nut-and-bolt assemblies are disposed in elongated slots in the blocks and cooperate with associated clamping members to clamp the Steinmann pins to the blocks after adjustment in two orthogonal directions and optional resilient bending of the pins.

3 Claims, 2 Drawing Figures

DEVICE FOR EXTERNAL FIXATION OF BONE FRAGMENTS

BACKGROUND OF THE INVENTION

This invention relates to a device for the reduction of bone fractures of the type having pins intended to be inserted in groups into the portions of bone to be mutually fixed or realigned, the pins being connected by sliding universal articulated couplings to at least one rigid tie-rod.

External fixation devices are illustrated and described, for example, in catalogue No. HJ 1012 E published in April, 1977, by Ets Jaquet Freres, Geneva, Switzerland, entitled "Osteotaxis ®".

SUMMARY OF THE INVENTION

It is an object of this invention to provide a device of this type which is more simply constructed, easier to handle, and lighter in weight.

A further object of this invention is to provide such a device which ensures a more stable connection between the pins (so-called Steinmann pins) and the bone fragments to be realigned.

To this end, in the device according to the present invention, the improvement comprises a plurality of sliding universal articulated couplings, each including a T-shaped member having two arms exhibiting respective longitudinal slots, clamping means cooperating with associated nut-and-bolt assemblies disposed in each of the slots for adjustably clamping and unclamping end portions of the pins to the arms of the T-shaped member, a spherical adapter sleeve split by staggered slots and slidingly mounted on the tie-rod, a coupling locking clamp comprising a ring portion having a spherical-shaped inner clamping surface embracing and fitted to the adapter sleeve and two straight end portions to which clamp lugs having respective screw holes are integrally affixed, and a further nut-and-bolt assembly traversing the clamp lugs through the screw holes for securing the coupling locking clamp to the upright of the T-shaped member and, when tightened, for simultaneously preventing both swivelling of the coupling locking clamp and the T-shaped member about the center of the spherical adapter sleeve and sliding of the adapter sleeve, together with the coupling locking clamp and the T-shaped member, along the tie-rod.

In a preferred embodiment of the invention, one side of the upright of the T-shaped member includes a recess fitted for receiving one of the clamp lugs. In addition, the tie-rod or tie-rods may be tubular.

BRIEF DESCRIPTION OF THE DRAWINGS

This preferred embodiment of the invention will now be described in detail with reference to the accompanying drawings, in which.

DESCRIPTION OF THE PREFERRED EMBODIMENT

Figure 1:
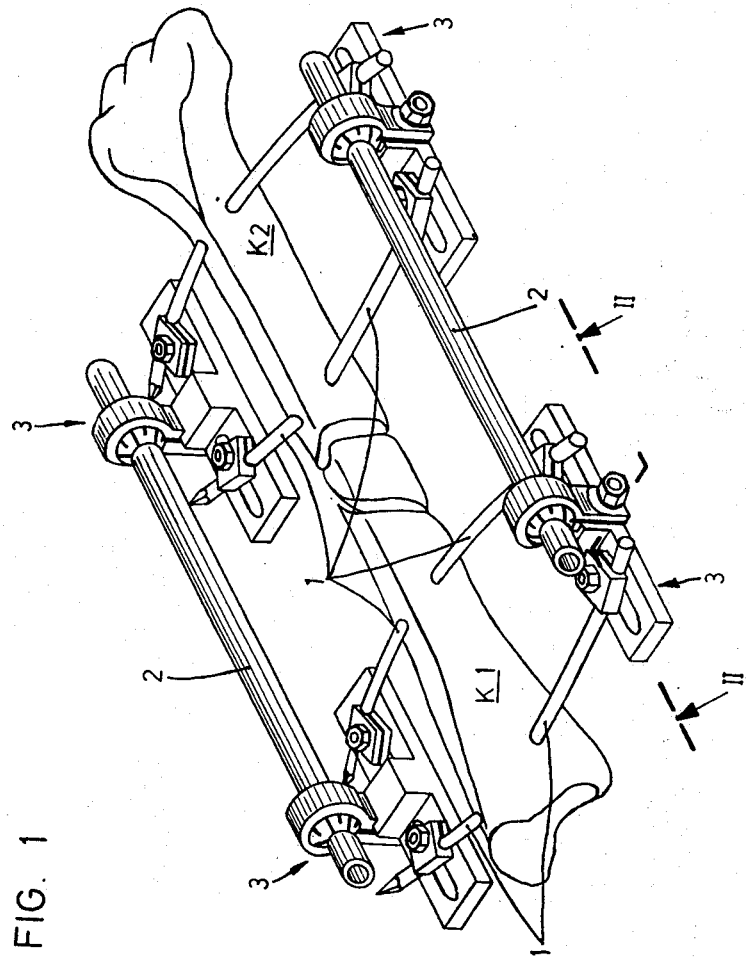
FIG. 1 is a perspective view of a device according to the present invention for the reduction of fractures.

The overall construction of the device illustrated in FIG. 1 is similar to that of the device shown on the cover of the above-mentioned catalogue. In both cases, it is one of a plurality of possible mountings which can be produced with a greater or lesser number of the various elements, as will be evident from the other illustrations in the catalogue.

Resiliently flexible pins 1 (Steinmann pins), intended for insertion in the bone portions K1, K2 to be mutually fixed or realigned, are connected to rigid tie-rods 2 by sliding universal articulated couplings 3. In order to achieve high bending resistance combined with light weight, tie-rods 2 take the form of stainless-steel tubes.

Figure 2:
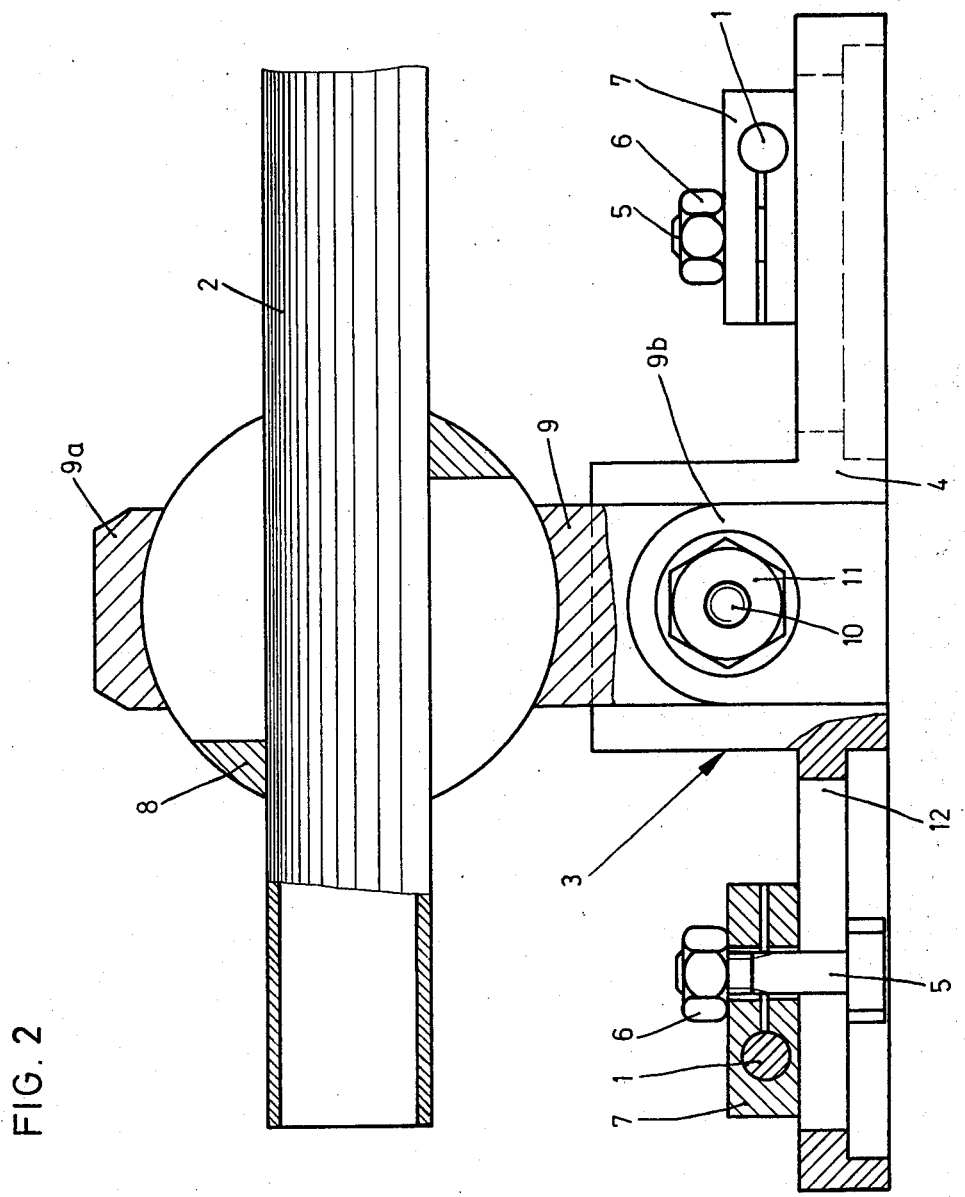
FIG. 2 is a side elevation view in partial section taken along the line II-II of FIG. 1 of one of the sliding universal articulated couplings utilized in the device.

Each coupling 3(FIG. 2) is made up of a T-shaped block 4, nut-and-bolt assemblies 5 & 6, clamping members 7, an adapter sleeve 8, a coupling locking clamp 9, and a nut-and-bolt assembly 10 & 11.

T-shaped block 4 has elongated slots 12 in its arms for the passage of bolts 5, which, together with nuts 6 and clamping members 7, make it possible to clamp pins 1 to block 4; a continuously-variable mutual adjustment can be carried out in two orthogonal directions prior to such clamping. Adapter sleeve 8 is split by staggered slots for increasing its radial elasticity, is spherical in shape, and is slidingly fitted on the smooth surface of tie-rod 2. Coupling locking clamp 9 comprises an open ring portion 9a embracing adapter sleeve 8 with a spherical-shaped inner surface fitted thereto, and two end portions to which clamp lugs 9b having holes for bolt 10 are integrally affixed; bolt 10 also passes through the upright of T-shaped block 4, which has a lateral recess fitted for receiving one of the two clamp lugs 9b, so that coupling locking clamp 9 is secured on block 4 against rotation about bolt 10. By tightening nut 11, ring portion 9a is pressed against adapter sleeve 8, and the latter in turn against tie-rod 2, so that tie-rod 2 is firmly coupled to block 4. Beforehand, however, any desired adjustments may be made about the center of spherical adapter sleeve 8 and along tie-rod 2 in the course of reducing the fracture. thus neutralization, compression, or distraction of the bone fragments may easily be effected and fixation secured. By means of the sliding displacement of clamping members 7 on the arms of block 4 prior to tightening of nuts 6, two important effects can be achieved:

(1) If so desired, the relaxed, straight Steinmann pins 1 can be subjected to bending stress, as shown in FIG. 1, whereby they are prevented from unintentionally slipping in the holes drilled in bone portions K1, K2.

(2) After the associated clamping members 7 on the respective blocks 4 have been tightened, the pins 1 situated in each of the bone fragments K1 and K2 are no longer parallel, and together with blocks 4 and clamping members 7, they form a kind of stiff truss structure; the two truss structures rigidly interconnected by the two tie-rods 2 hold bone portions K1 and K2 immovably fast to one another when they are subjected to axial stress, e.g., by the weight of the patient. Hence, the patient can be put "back on his feet" quite soon after a fracture of the femur or tibia has been reduced, even when a comminuted fracture is involved.

While specific embodiments of the present invention have been shown and described in the specification and drawings to illustrate and explain the present invention, it should be understood that the present invention is not limited to these specific embodiments, but contemplates other embodiments falling within the scope of the following claims.

What is claimed is:

1. A device for the reduction of bone fractures, of the type having pins intended to be inserted in groups into portions of bone to be mutually fixed or realigned, said pins being connected by sliding universal articulated couplings to at least one rigid tie-rod, said device comprising a plurality of said couplings, each coupling including

- a T-shaped member having two arms exhibiting respective longitudinal slots,
- two nut-and-bolt assemblies respectively disposed in said slots,
- clamping means cooperating with each of said nut-and-bolt assemblies for adjustably clamping and unclamping end portions of said pins to said two arms,
- a spherical adapter sleeve split by staggered slots and slidingly mounted on said tie-rod,
- a coupling locking clamp comprising a ring portion having a spherical-shaped inner clamping surface embracing and fitted to said adapter sleeve and two straight end portions to which clamp lugs having respective screw holes are integrally affixed, and
- a further nut-and-bolt assembly traversing said clamp lugs through said screw holes for securing said coupling locking clamp to the upright of said T-shaped member and, when tightened, for simultaneously preventing both swivelling of said coupling locking clamp and said T-shaped member about the center of said spherical adapter sleeve and sliding of said adapter sleeve, together with said coupling locking clamp and said T-shaped member, along said tie-rod.

2. The device of claim 1, wherein one side of the upright of said T-shaped member includes a recess fitted for receiving one of said clamp lugs.

3. The device of claim 1 or claim 2, wherein said at least one tie-rod is tubular.

* * * * *